United States Patent [19]

Weischedel

[11] Patent Number: 5,414,353
[45] Date of Patent: May 9, 1995

[54] METHOD AND DEVICE FOR NONDESTRUCTIVELY INSPECTING ELONGATED OBJECTS FOR STRUCTURAL DEFECTS USING LONGITUDINALLY ARRANGED MAGNET MEANS AND SENSOR MEANS DISPOSED IMMEDIATELY DOWNSTREAM THEREFROM

[75] Inventor: Herbert R. Weischedel, South Windsor, Conn.

[73] Assignee: NDT Technologies, Inc., South Windsor, Conn.

[21] Appl. No.: 61,450

[22] Filed: May 14, 1993

[51] Int. Cl.$^6$ .............. G01N 27/72; G01N 27/82; G01R 33/12
[52] U.S. Cl. .................... 324/232; 324/238
[58] Field of Search .............. 324/227, 238, 239, 240, 324/241, 232

[56] References Cited

U.S. PATENT DOCUMENTS

| | | | |
|---|---|---|---|
| 4,331,919 | 5/1982 | Beckley | 324/240 |
| 4,495,465 | 1/1985 | Tomaiuolo et al. | 324/232 |
| 4,659,991 | 4/1987 | Weischedel . | |
| 4,675,604 | 6/1987 | Moyer et al. | 324/240 |
| 4,827,215 | 5/1989 | van der Walt . | |
| 4,855,676 | 8/1989 | Cecco et al. | 324/232 |
| 4,929,897 | 5/1990 | Van der Walt | 324/232 |
| 5,036,277 | 7/1991 | Van der Walt | 324/232 |
| 5,198,765 | 3/1993 | Van Der Walt | 324/227 |

FOREIGN PATENT DOCUMENTS

| | | | |
|---|---|---|---|
| 936033 | 9/1963 | United Kingdom | 324/232 |
| 492704 | 11/1979 | U.S.S.R. | 324/232 |

OTHER PUBLICATIONS

German article Die elektroMagnetische Prüfung von *Drahtseilen* by Urs Balthasar Meyer (1973).
Nondestructive Testing Handbook, vol. 4, "Electromagnetic Testing:, Eddy Current, Flux Leakage and Microwave Nondestructive Testing," pp. 212–215 (1986).

*Primary Examiner*—Sandra L. O'Shea
*Assistant Examiner*—R. Phillips
*Attorney, Agent, or Firm*—McCormick, Paulding & Huber

[57] ABSTRACT

A magnetic inspection device for detecting structural faults in elongated magnetically permeable objects has two opposite magnetic poles, at least one pole being an end pole, that induce a first magnetic flux axially in a first section of an object between the poles, and an oppositely directed magnetic flux in another section adjacent the end pole. As the device and object move relative to one another, eddy currents induced in the object by the changing longitudinal fluxes at the end pole are detected to locate structural faults in the object.

24 Claims, 3 Drawing Sheets

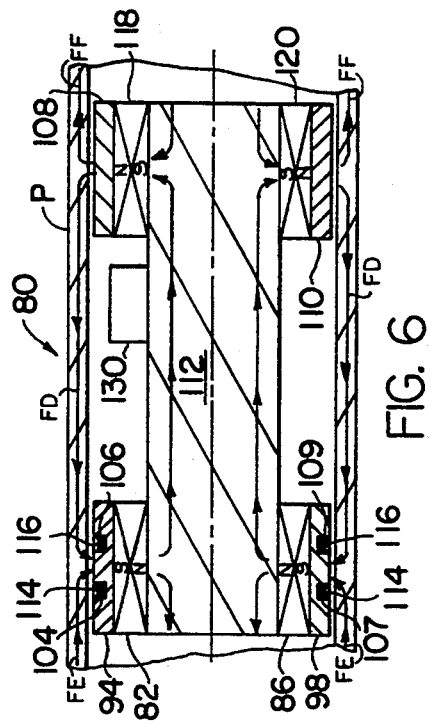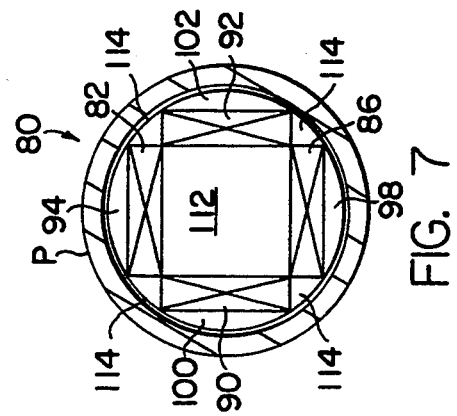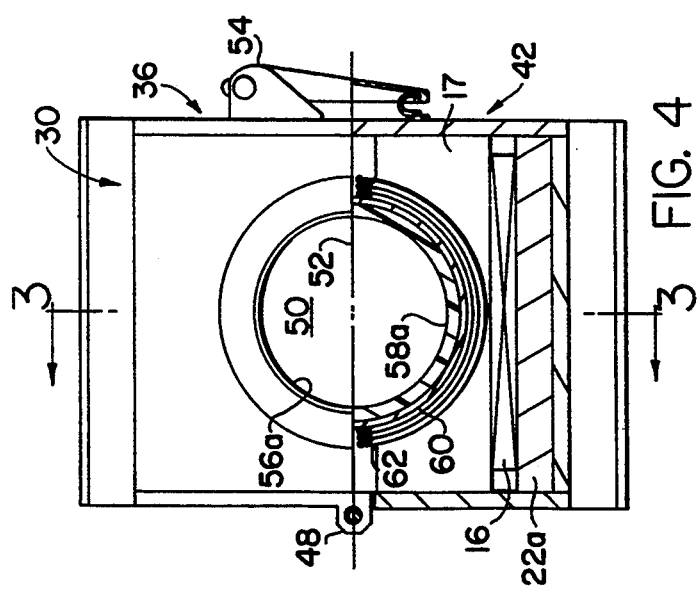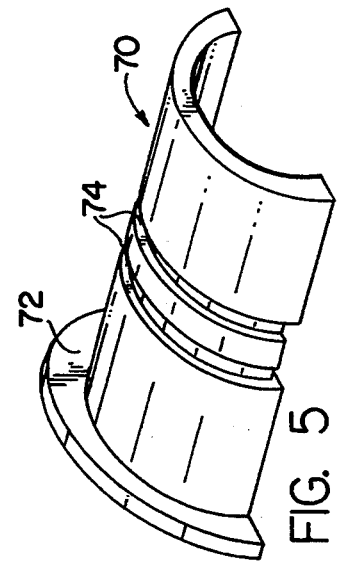

METHOD AND DEVICE FOR NONDESTRUCTIVELY INSPECTING ELONGATED OBJECTS FOR STRUCTURAL DEFECTS USING LONGITUDINALLY ARRANGED MAGNET MEANS AND SENSOR MEANS DISPOSED IMMEDIATELY DOWNSTREAM THEREFROM

BACKGROUND OF THE INVENTION

The present invention relates to an inspection device and a method for nondestructive inspection and evaluation of magnetically permeable elongated objects such as wire cables, rods, pipes, and the like. The invention is concerned more particularly with a magnetic inspection method and device for detecting structural faults in the objects.

Presently, wire cables, pipes and the like can be inspected for three types of defects. Each of the defects is described in detail below and is an important indicator of structural integrity of the elongated object.

First, the elongated object can be inspected for a distributed defect known as a loss of metallic cross-sectional area (LMA). The loss of metallic cross-sectional area in a cable or pipe may be due to corrosion, wear or abrasion.

Second, the elongated object can be inspected for a defect known as a localized fault (LF) such as broken wires within a cable or circumferential cracks along a wall of a gas pipe.

Third, the elongated object can be inspected for a defect known as a structural fault (SF). For example, structural faults in a pipe include longitudinal stress-corrosion cracks in the pipe wall, and hard spots. Likewise, in a wire cable structural faults include changes in wire contact patterns such as loose wires.

Magnetic inspection methods for detecting LMA and LF in elongated magnetically permeable objects are presently available. For example, my U.S. Pat. No. 4,659,991 uses a method to nondestructively, magnetically inspect an elongated magnetically permeable object for LMA and LF. The method induces a saturated magnetic flux through a section of the object between two opposite magnetic poles of a magnet means. The saturated magnetic flux within the object is directly related to the cross-sectional area of the magnetically permeable object. A magnetic flux sensing coil is positioned between the poles near the surface of the object and moves with the magnet means relative to the object in order to sense quantitatively the magnetic flux contained within the object.

Because of the direct relationship between the cross-sectional area and the magnetic flux contained within the magnetically saturated object, LMA is detected by connecting the magnetic flux sensing coil to an electronic integrator. Likewise, a magnetic leakage flux sensing coil is also positioned between the poles near the surface of the object and moves with the magnet means relative to the object in order to sense qualitatively magnetic leakage flux escaping the object because of a distortion in magnetic flux caused by a localized fault within the object. LF is detected by a differential magnetic leakage flux sensing coil.

Employing magnetic inspection devices for detecting distributed defects such as structural faults, however, has not been successful using the method described above. Structural defects, such as longitudinal stress-corrosion cracks in pipes or loose wires in wire ropes, usually do not produce sufficient magnetic leakage flux to be detectable by magnetic sensors.

The reason for the detection failure is that a structural fault does not necessarily entail a detectable loss in metallic cross-sectional area. For example, loose wire contact patterns in a wire cable are indicative of a loss in structural integrity but not necessarily indicative of a detectable loss in cross-sectional area. New methods are needed to overcome the problem of reliably detecting distributed structural faults in elongated objects.

One solution employs an eddy current technique as opposed to magnetic/leakage flux techniques. U.S. Pat. No. 4,827,215 addresses the problem of detecting structural faults in wire cable by a device employing a three pole magnet. The device has two end poles of the same polarity with an opposite polarity-shared common pole centered between the two end poles. The purpose of the three pole magnet is to induce two opposing longitudinal, saturated magnetic fields in adjacent sections of a wire rope, each magnetic field associated respectively with one of two adjacent sections of the wire cable and the common pole, and each of the two longitudinal fields extending to a different end pole. Adjacent the common pole, the wire cable experiences a change in direction of the longitudinal magnetic flux. A stagnation point is defined as the longitudinal location in the object where the longitudinal magnetic flux is zero as the flux changes in direction.

Because of Faraday's Law, eddy currents are generated in the wire cable near the common pole because of the change of the longitudinal magnetic flux experienced in the object as it moves relative to the magnetic inspection device. According to Lenz's Law, the eddy currents generate another magnetic flux that opposes the change of the longitudinal magnetic flux induced by the magnets. Because eddy currents are a function of the electromagnetic properties of the wire cable or pipe, any structural fault will correspondingly change the eddy current patterns. Change of the eddy current patterns in turn correspondingly changes the normally constant opposing magnetic flux generated by the eddy currents. This change of the opposing magnetic flux can be detected by magnetic sensors such as coils or Hall generators. Hence, a sensor located at the common pole can detect changes in the eddy currents owing to structural faults in the object. In addition, the location of a sensor at the stagnation point is conducive to measuring changes in eddy currents because of minimum interference from longitudinal magnetic flux induced by the magnets since the longitudinal magnetic flux is virtually zero at the common pole and the stagnation point.

The inspection device described in U.S. Pat. No. 4,827,215 uses an eddy current technique, but the existence of eddy currents in the context of magnetic inspection devices is known in the field. For example, a 1983 Swiss paper Die elektromagnetische Prüfung von Drahtseilen by Urs Balthasar Meyer mentions eddy currents as parasites because they distort the longitudinal magnetic flux.

A problem with the above-mentioned magnetic inspection device is that the device uses a bulky three pole magnet. This prior art overlooks the fact that changing longitudinal magnetic flux for inducing eddy currents and a corresponding stagnation point for favorable sensor positioning is also present at an end pole. The existence of changing longitudinal magnetic flux and a corresponding stagnation point at an end pole allows the construction of a simpler magnetic inspection device for the detection of structural faults.

Accordingly, it is a general object of the present invention to provide a simpler method and apparatus for determining structural faults in a magnetically permeable elongated object. Structural faults such as longitudinal stress-corrosion cracks, hard spots, manufacturing flaws, residual stress or stress caused by bending or sagging in a pipe, and wire contact pattern changes in a wire cable caused by loose wires are more easily detected by the described method.

It is another object of the present invention to provide an eddy current-magnetic saturation method which significantly reduces background noise so as to detect structural faults with improved sensitivity.

In addition, it is a general object of the present invention to employ a method and apparatus that can be employed for detecting structural faults inside or outside an elongated object.

SUMMARY OF THE INVENTION

The present invention resides in a magnetic inspection method and device for nondestructively detecting structural faults in elongated objects such as wire cables, rods, pipes, and the like.

One embodiment of a magnetic inspection device which carries out the method comprises magnet means having two opposite magnetic poles spaced from one another for positioning at longitudinally spaced stations along an elongated magnetically permeable object and for movement longitudinally relative to the object. The magnet means defines first and second magnetic flux circuits. The first magnetic flux circuit has a forward portion extending between one pole and the other pole through a first section of the elongated object between the stations, and the first magnetic flux circuit has a return portion extending through a ferromagnetic flux return path within the magnet means, whereby a first longitudinal magnetic flux is induced in one direction generally at a magnetic saturation level through the elongated object. The second magnetic flux circuit has a forward portion extending through a second section of the elongated object lying adjacent both the first section and the one pole. The forward portion of the second magnetic flux circuit extends in a direction opposite to that of the forward portion of the first magnetic flux circuit. The second magnetic flux circuit has a return portion externally of the elongated object, whereby a second longitudinal magnetic flux is induced in the object in a direction opposite to that of the first longitudinal magnetic flux. The junction of the two oppositely directed magnetic fluxes in a moving portion of the object confronting the one pole defines a stagnation point where the magnitude of the first and second longitudinal magnetic fluxes is zero, and where eddy currents are generated on the surface of the moving portion of the object because of change of longitudinal magnetic flux. The generated eddy currents dissipate as the portion moves downstream in the direction of object movement from the one pole to the other pole. An eddy current change detecting means is associated with the one pole for positioning adjacent to the object where the longitudinal magnetic flux is at or approaching a magnetic saturation level and where eddy currents generated by the change of longitudinal magnetic flux have not substantially dissipated within the moving portion as the portion passes the eddy current change detecting means so as to detect longitudinal magnetic flux changes from the moving portion of the object as the portion moves past the eddy current change detecting means, whereby longitudinal magnetic flux changes experienced by the moving portion of the object passing by the eddy current change detecting means generate a first signal in the eddy current change detecting means including a first signal component originating from eddy current changes representative of structural faults and a second signal component originating from magnetic flux changes representative of loss of metallic cross-sectional area or localized faults. A magnetic flux detecting means is associated with the other of the poles for positioning downstream in the direction of object movement from the eddy current change detecting means and adjacent to the object where the longitudinal magnetic flux is at or approaching a magnetic saturation level and where the eddy currents generated by the change of longitudinal magnetic flux have substantially dissipated within the moving portion as the portion passes the magnetic flux detecting means so as to detect longitudinal magnetic flux changes experienced by the moving portion of the object passing by the magnetic flux detecting means after the portion has moved past the eddy current change detecting means, whereby longitudinal magnetic flux changes of the moving portion generate a second signal in the magnetic flux detecting means including a third signal component originating from eddy current changes representative of structural faults and a fourth signal component originating from magnetic flux changes representative of loss of metallic cross-sectional area or localized faults. A digital processing means determines the location and magnitude of a structural fault within the moving portion from the first and second signals.

Another embodiment of the magnetic inspection device which carries out the method is an internal magnetic inspection device for nondestructively detecting structural faults from within elongated objects, such as pipes and the like. The internal device comprises magnet means including two opposite magnetic poles for mounting adjacent to the interior surface of an elongated object. The poles are spaced from one another for positioning at longitudinally spaced stations adjacent the object during movement longitudinally relative to the object. The magnet means defines first and second magnetic flux circuits. The first magnetic flux circuit has a forward portion extending from one pole to the other pole through a first section of the elongated object between the stations. The first magnetic flux circuit has a return portion through a ferromagnetic flux return path within the magnet means to be disposed at or near the central longitudinal axis of the object to be inspected and extending from the one pole to the other pole, whereby a first longitudinal magnetic flux is induced in one direction through the elongated object. The second magnetic flux circuit has a forward portion extending from the one pole through a second section of the elongated object lying adjacent both the first section and the one pole in a direction opposite to that of the forward portion of the first magnetic flux circuit, and a return portion externally of the elongated object whereby a second longitudinal magnetic flux is induced in the object in a direction opposite to that of the first longitudinal magnetic flux. The junction of the two oppositely directed magnetic fluxes is in a portion of the object confronting the one pole and defines a stagnation point. A magnetic flux sensing coil is located near the one pole and close to the interior surface of the elongated object to be inspected for detecting eddy current changes representative of structural faults during relative movement of the magnet means and the object.

Another aspect of the present invention relates to a method for nondestructively inspecting an elongated object such as wire cables, rods, pipes, and the like, for structural faults. The method comprises the steps of inducing a first magnetic flux in one direction generally at a saturation level by means of a magnet device through a first longitudinal section of an elongated object. The longitudinal section extends between first and second longitudinally spaced opposite poles of the magnet device. A second magnetic flux is induced through a second longitudinal portion of the object adjacent the first longitudinal portion by means of the magnet device. The second magnetic flux is opposite in direction to that of the first magnetic flux. The junction of the first and second magnetic fluxes in the object is adjacent the first pole and defines a stagnation point. The magnet device and the induced first and second magnetic fluxes are moved progressively and longitudinally relative to the object so as to induce circumaxial eddy currents in a moving portion of the object passing the first pole due to the change in the magnetic fluxes within the moving portion of the magnetically permeable object at the first pole of the magnet device. The first pole of the magnet device is upstream from the second pole of the magnet device relative to movement of the object. A first signal is generated from the moving portion of the object when the portion is immediately downstream from the first pole of the magnet device in the direction of movement of the object during the moving step. The moving portion of the object during the step of generating a first signal is at or approaching a magnetic saturation level and includes substantial eddy currents. The first signal includes a first signal component originating from eddy current changes representative of structural faults and a second signal component originating from magnetic flux changes representative of loss of metallic cross-sectional area or localized faults. A second signal is subsequently generated from the moving portion of the object when the portion is immediately upstream from the second pole of the magnet device in the direction of movement of the object during the moving step. The moving portion of the object during the step of generating a second signal is at or approaching a magnetic saturation level and includes eddy currents which have substantially dissipated during the time elapsed from the step of generating a first signal. The second signal includes a third signal component originating from eddy current changes and a fourth signal component originating from magnetic flux changes. The location and magnitude of a structural fault within the moving portion is determined from the first and second signals.

BRIEF DESCRIPTION OF THE DRAWINGS

FIG. 1b is a graph illustrating magnetic flux induced in the section of the pipe by the inspection device in FIG. 1a.

FIG. 4 is an end view of the device in FIGS. 2-3 partially sectioned along the sectioning line 4—4 of FIG. 3.

FIG. 5 is a perspective view of a plastic bushing with grooves for supporting a magnetic flux sensing coil in another embodiment of the invention.

FIG. 6 is a view of another embodiment of the present invention within a pipe.

FIG. 7 is an end view of the device within the pipe in FIG. 6.

DESCRIPTION OF THE PREFERRED EMBODIMENTS

Figure 1A:
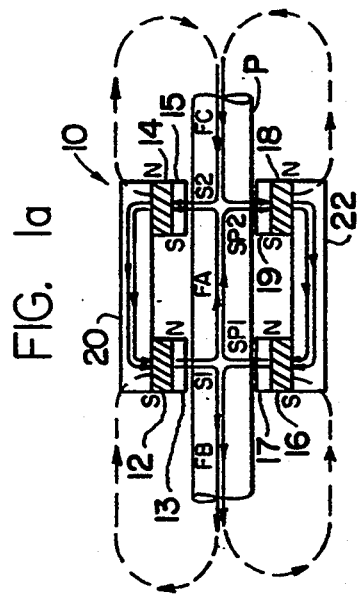
FIG. 1a schematically illustrates an embodiment of the magnetic inspection device along a longitudinal section of a metal pipe.

FIG. 1a illustrates schematically the operation of one preferred embodiment of a magnetic inspection device 10 for nondestructively inspecting a magnetically permeable elongated object such as a wire cable or a pipe P for structural faults. In the case of a pipe, structural faults can occur because of longitudinal cracks in the pipe wall, hard spots, manufacturing flaws, residual stress and pipe stress such as bending and sagging.

The magnetic inspection device 10 is shown with a set of oppositely poled permanent end pole magnets 12,14 disposed along one lateral side of the pipe P at stations S1 and S2 respectively. The magnets 12,14 are positioned adjacent respective pole pieces 13,15. Further, the magnets 12,14 are connected by a ferromagnetic bar 20 completing a magnetic flux circuit having a forward portion through the pipe P between the stations S1 and S2, and a return portion through the bar 20. The magnets 12,14 induce part of longitudinal magnetic flux FA in the section of the pipe between the stations S1 and S2.

Similarly, the magnet device 10 has another set of oppositely poled permanent end pole magnets 16,18 disposed along a side of the pipe P opposite that of magnets 12,14 respectively. The magnets 16,18 are positioned adjacent respective pole pieces 17,19. Further, the magnets 16,18 are connected by a ferromagnetic bar 22 completing a magnetic flux circuit having a forward portion through the pipe P between the stations S1 and S2, and a return portion through the bar 22. The magnets 12 and 16 have like poles adjacent the pipe and the magnets 14 and 18 have like poles adjacent the pipe so that the magnets 16,18 reinforce the longitudinal magnetic flux FA between the stations S1 and S2 preferably to a saturation level.

In addition, the end pole magnet 12 at the station S1 induces part of longitudinal magnetic flux FB within the pipe in a direction opposite to that of the saturated magnetic flux FA. The longitudinal magnetic flux FB is induced in a magnetic flux circuit having a forward portion extending through a section of the pipe P which is adjacent both the section of the pipe P between the stations S1 and S2 and the end pole magnet 12. The magnetic flux circuit has a return portion externally of the pipe P through the surrounding medium. Likewise, the end pole magnet 16 at the station S1 induces part of the longitudinal magnetic flux FB in a magnetic flux circuit through the same section of the pipe as does the end pole magnet 12. The magnetic flux circuit also has a return portion externally of the pipe P through the surrounding medium.

By symmetry, the end pole magnet 14 at the station S2 induces part of longitudinal magnetic flux FC within the pipe in a direction opposite to that of the saturating longitudinal magnetic flux FA. The longitudinal magnetic flux FC is induced in a magnetic flux circuit having a forward portion extending through a section of the pipe P which is adjacent both the section of the pipe P between the stations S1 and S2 and the end pole magnet 14. The magnetic flux circuit has a return portion externally of the pipe P through the surrounding medium. Likewise, the end pole magnet 18 at the station S2 induces part of the longitudinal magnetic flux FC in a magnetic flux circuit through the same section of the pipe as does the end pole magnet 14. The magnetic flux circuit also has a return portion externally of the pipe P through the surrounding medium. The change in direction of the longitudinal magnetic fluxes FA and FB in the pipe P at the station S1 at the end pole magnets 12,16 defines a stagnation point SP1 where the magnitude of the longitudinal component of both fluxes FA and FB is zero. Likewise the change in direction of the longitudinal magnetic fluxes FA and FC in the pipe P at station S2 at the end pole magnets 14,18 defines a stagnation point SP2 where the magnitude of the longitudinal component of both FA and FC is zero. The stagnation points and the reversal in the direction or polarity of the longitudinal magnetic flux is illustrated graphically in FIG. 1b.

Because of Faraday's Law, when the pipe P moves relative to the magnets 12,14,16,18 at speeds from 100 fpm up to and possibly greater than 18 mph (1584 fpm), the rapid change in the longitudinal magnetic flux at either station induces circumferential eddy currents of significant magnitude in the pipe. Because of Lenz's Law, a normally constant magnetic flux is induced by the eddy currents which opposes the change in magnetic flux induced by the magnets. The magnitude of the circumferential eddy currents is a function of the conductive properties of the pipe P. A structural fault such as a longitudinal crack in a pipe or loose wires in a wire rope alters the conductive properties on a circumferential path along a surface of the pipe P. As a result, the altered properties change the magnitude of normally steady circumferential eddy currents and the opposing magnetic flux induced by the eddy currents. The eddy current changes thus become a measure of the structural faults in the pipe. For example, eddy current change detecting means such as Hall effect sensors or magnetic flux sensing coils can be located near the end poles, such as the end poles located in this instance at the station S1, in order to detect eddy current changes resulting from structural faults in the pipe as it moves relative to the device 10.

Figure 1B:
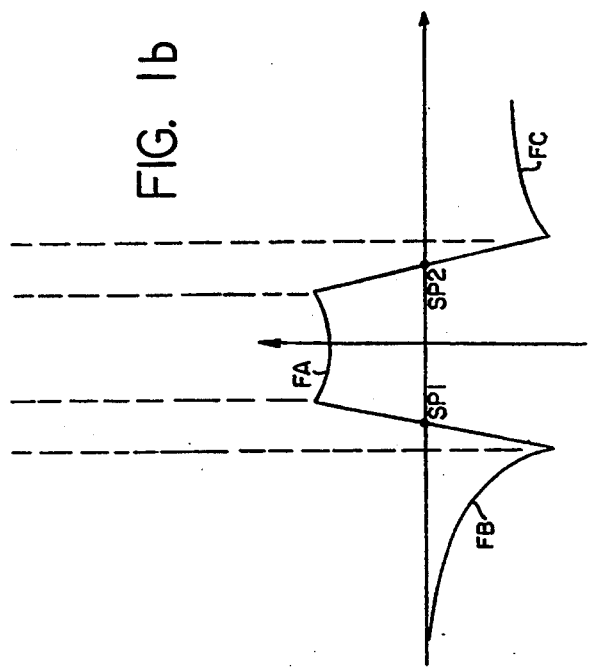

The graph of FIG. 1b illustrates the longitudinal magnetic flux induced in the section of the pipe P by the end pole magnets of the magnetic inspection device in FIG. 1a as the pipe moves in a direction from left to right with respect to the device. A rapid reversal in the longitudinal magnetic flux induced by the magnets 12,16 occurs at the stagnation point SP1 and creates eddy currents in a portion of pipe P confronting the pole pieces 13,17 of the one set of end poles. A similar rapid reversal in the longitudinal magnetic flux induced by the magnets 14,18 but opposite in sense occurs at the stagnation point SP2 and creates eddy currents in a portion of the pipe confronting the pole pieces 15,19 of the other set of end poles. The eddy current change detecting means positioned near either one of the end pole stations detects changes in the otherwise steady eddy currents induced in a portion of the pipe confronting the end pole, when a structural fault passes by the end pole.

The magnetic inspection device 10 need not be limited to the detection of structural faults. The inspection device may include LMA and/or LF sensors as described in my above-referenced U.S. Pat. No. 4,659,991 located between the stations S1 and S2 where the induced longitudinal magnetic flux FA is saturated. In addition, the magnetic inspection device is not limited to a two pole device, and therefore, the eddy current change detecting means can be employed at the end pole of a device with more than two poles.

Figure 3:
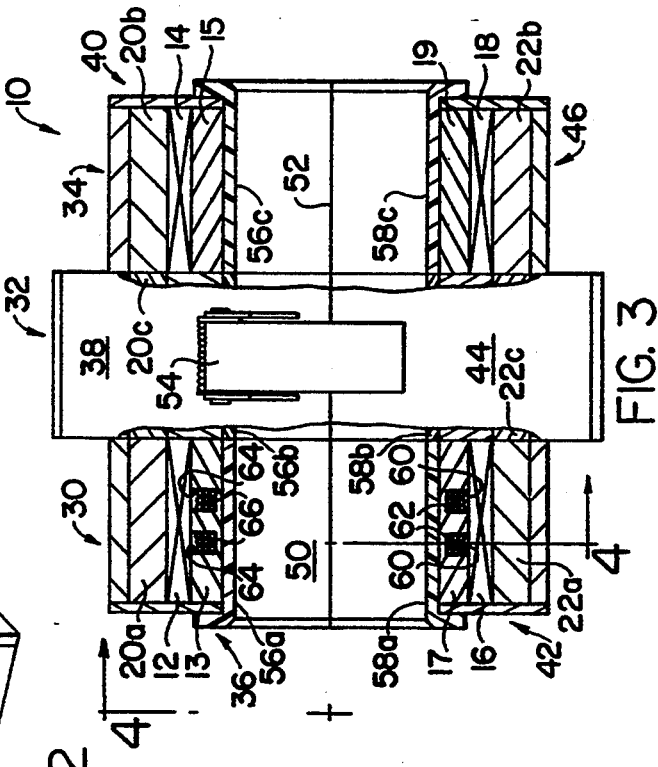
FIG. 3 is an elevation view of the device in FIG. 2 partially sectioned along the sectioning line 3—3 of FIG. 4.
Figure 2:
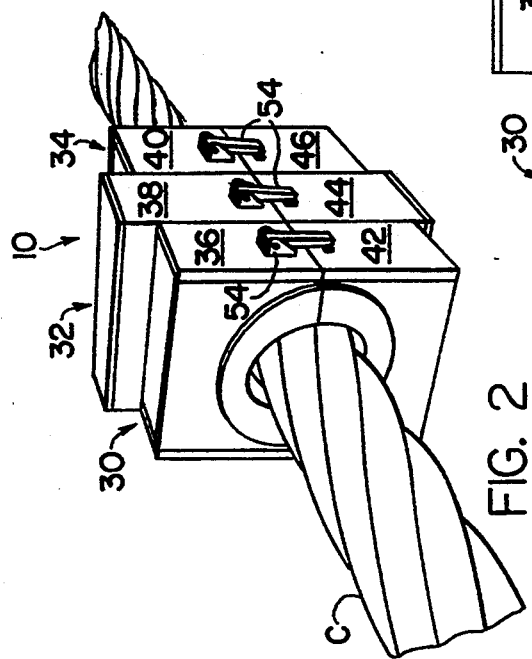
FIG. 2 is a perspective view of an embodiment of the magnetic inspection device mounted on a metal cable to be inspected.

FIGS. 2–4 disclose the structural details of one embodiment of the magnetic inspection device shown schematically in FIG. 1a. In FIG. 2, the magnetic inspection device 10 is comprised of three separate housing portions 30,32,34. Each housing portion is divided into an upper housing half 36,38 or 40 and a lower housing half 42,44 or 46. The upper housing halves 36,38,40 are respectively connected to the lower housing halves 42,44,46 by hinges 48,48,48, one of which is shown in FIG. 4. The upper housing halves 36,38,40 and the lower housing halves 42,44,46 define a central passageway 50 shown in FIGS. 3–4 through which an elongated magnetically permeable object such as a pipe or, in this instance, a cable C may move longitudinally of itself during inspection. In addition, the upper housing halves 36,38,40 and the lower housing halves 42,44,46 also define a parting plane 52 shown in FIGS. 3–4 that intersects the central passageway along its length to permit the upper housing halves 36,38,40 and the lower housing halves 42,44,46 to be mounted in mating relationship over and be removed from the cable C intermediate the ends of the cable. The upper housing half 36 and the lower housing half 42 of the housing portion 30 are secured in place and retained in a closed position by a draw latch 54. The upper housing half 38 and the lower housing half 44 of the housing portion 32 are similarly secured in place and retained in a closed position by a second draw latch 54. The upper housing half 40 and the lower housing half 46 of the housing portion 34 are also secured in place and retained in a closed position by a third draw latch 54. The draw latches 54,54,54 are located on the side of the magnetic inspection device 10 opposite the respective hinges 48,48,48. The housing portions 30,32,34 may be integrated or separable as defined more specifically in my U.S. patent application Ser. No. 07/888,587 filed May 26, 1992.

FIGS. 3–4 show the interior structure of the magnetic inspection device 10 of FIG. 2. In the lower housing halves 42,44,46 the pole piece 17 is located on the lower side of the central passageway 50 within lower housing half 42 and is in contacting relationship with the magnet 16 which is polarized radially relative to the central passageway. The side of the pole piece 17 adjacent the passageway 50 is arcuately shaped so as to conform to the circular passageway 50. The pole piece 17 contains two parallel grooves 60 that extend circumaxially in a semi-circular arc about a lower half of the central passageway. The grooves 60 support a yoke-shaped magnetic flux sensing coil 62 close to the surface of a cable being inspected to detect changes in eddy currents at the surface of the cable.

Similarly, on the lower side and at the opposite end of the passageway 50 within the lower housing half 46, the pole piece 19 is in contacting relationship with the magnet 18 which is also polarized radially relative to the central passageway 50 but with a polarity opposite to that of the magnet 16. The side of the pole piece 19 adjacent the passageway 50 is arcuately shaped so as to conform to the circular passageway 50.

Each magnet 16,18 is connected by a ferromagnetic bar 22a or 22b which resides within each lower housing half 42 or 46. The bars 22a and 22b are magnetically coupled through intermediate bars 22c residing within the lower housing half 44 to form a complete magnetic flux path through the lower housing halves 42,44,46. The ferromagnetic bars 22a,22b,22c provide the magnetic flux return path for the magnetic flux induced by the permanent magnets 16,18.

The lower half of the passageway 50 is lined with semi-circular plastic bushings 58a,58b,58c within the respective lower housing halves to form a low friction guide for the object as it moves through the passageway.

In symmetrical fashion, referring to the structure contained within the upper housing halves 36,38,40, the pole piece 13 is located on the upper side of the central passageway 50 opposite to the pole piece 17 and within the upper housing half 36. The pole piece 13 is in contacting relationship with the magnet 12 which is polarized radially relative to the central passageway and with the same polarization as the magnet 16.

The pole piece 13 contains two parallel grooves 64 that extend circumaxially in a semi-circular arc about an upper half of the central passageway. The grooves 64 support a yoke-shaped magnetic flux sensing coil 66 close to the surface of a cable being inspected to detect changes in eddy currents. The side of the pole piece 13 adjacent the passageway 50 is arcuately shaped so as to conform to the passageway 50.

Similarly, on the upper side and at the opposite end of the passageway 50, the pole piece 15 within the upper housing half 40 is in contacting relationship with the magnet 14 which is also polarized radially relative to the central passageway 50 but of opposite polarity to that of the magnet 12. The side of the pole piece 15 adjacent the passageway 50 is arcuately shaped so as to conform to the circular passageway 50. Each magnet 12,14 is connected by a ferromagnetic bar 20a or 20b which resides within each upper housing half 36 or 40. The bars 20a and 20b are magnetically coupled through intermediate bars 20c residing within the upper housing half 38 to form a complete magnetic flux path through the upper housing halves 36,38,40. The ferromagnetic bars 20a,20b,20c provide the magnetic flux return path for the magnetic flux induced by the permanent magnets 12,14.

The upper half of the passageway 50 is lined with semi-circular plastic bushings 56a,56b,56c within the respective upper housing halves to form a low friction guide for the object as it moves through the passageway.

FIG. 5 shows a semi-circular plastic bushing 70 for lining the passageway of the inspection device in another embodiment of the invention. The bushing 70 has a mounting flange 72 and two circumferential grooves 74 for supporting a yoke-shaped magnetic flux sensing coil close to the surface of the object being inspected. In this embodiment the grooves 64 of FIG. 3 are unnecessary.

FIGS. 6–7 schematically illustrate another embodiment of the present invention using an internal magnetic inspection device 80 which is placed within a pipe P to be inspected. FIG. 7 is an end view of the pipe P and the magnetic inspection device 80. A first set of four permanent end pole magnets 82,86,90,92 are positioned in ninety degree relation to each other about one end of a four-sided ferromagnetic bar 112. The magnets 82,86,90,92 have inner sides in contacting relationship with the four sides of the bar 112 that is generally square in cross-section. The magnets 82,86,90,92 are radially polarized with the same radial polarization with respect to the ferromagnetic bar 112.

The inner sides of pole pieces 94,98,100,102 are respectively positioned on the outer sides of the magnets 82,86,90,92. The outer sides of the pole pieces 94,98,100,102 are of a convex, arcuate shape so as to conform to the inner surface of a pipe to be inspected. A plastic bushing may be positioned over the pole pieces in order to serve as a low friction guide as the internal inspection device 80 and pipe move relative to one another.

At the opposite end of the bar 112 shown in FIG. 6, are a second set of four radially polarized end pole magnets 118,120 (only two visible) having the same radial polarization with respect to the bar 112 but having a polarity opposite to that of the first set of magnets 82,86,90,92. As with the first set of magnets, the second set of magnets are similarly placed around the ferromagnetic bar with four respective pole pieces 108,110 (only two visible). The first and second sets of magnets induce a saturated magnetic flux FD in a magnetic flux circuit having a forward portion in a section of the pipe surrounding the device 80, and a return portion in the bar 112. The operation of the internal magnetic inspection device resulting from the above-mentioned structure now follows.

All the radially polarized magnets induce a generally saturated longitudinal magnetic flux FD in the section of pipe surrounding the device 80. The ferromagnetic bar 112 serves as a common magnetic flux return path to complete the magnetic flux circuit formed by the magnets.

As with the magnetic inspection device 10 illustrated in FIG. 1a, the inner magnetic inspection device 80 in FIG. 6 also induces longitudinal magnetic fluxes FE and FF in a direction opposite to that of FD. The longitudinal magnetic flux FE is induced in one of two sections of the pipe adjacent the section of the pipe surrounding the device 80. Likewise, the longitudinal magnetic flux FF is induced in another of the two sections. As in the case of the magnetic inspection device 10, stagnation points occur within portions of the pipe confronting the first and second sets of end pole magnets where the longitudinal component of the fluxes is zero. Two differential magnetic flux sensing coils 114 and 116 wrapped around the four pole pieces 94,98,100,102 and extending circumferentially of the pipe are placed in corresponding grooves 104,106 in pole piece 94, corresponding grooves 107,109 in pole piece 98, and corresponding grooves (not visible) in pole pieces 100 and 102 at one end of the inspection device 80 in order to detect eddy current changes which are representative of structural faults. The coils are coupled to telemetry apparatus 130 connected with the device 80 to transmit the detected changes to a remote monitoring station.

Figure 8A:
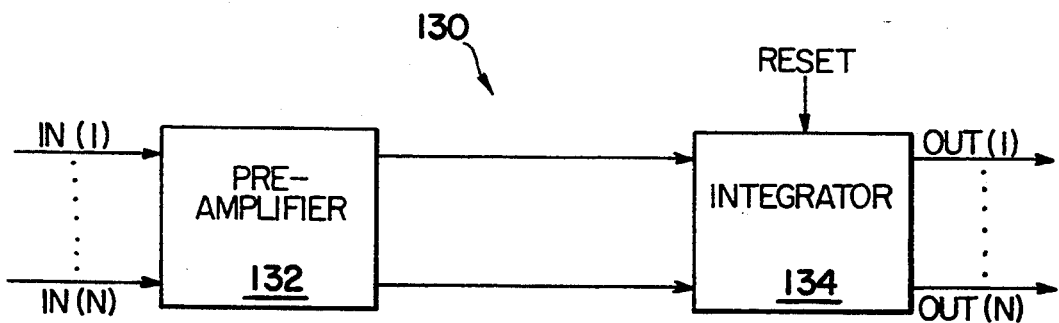
FIG. 8a is a schematic view of circuitry for individually integrating multiple voltage signals from sensing means employed circumaxially of an object to be inspected.

FIG. 8a schematically shows circuitry which processes voltage signals IN(1) through IN(N) each induced in distinct differential magnetic flux sensing coils (not shown). A pre-amplifier 132 boosts voltage signals IN(1) through IN(N). The signals are subsequently integrated by an electronic integrator 134 in order to quantitatively measure eddy current changes which are representative of structural faults.

Each sensing coil detects eddy current changes in a different axial location about a longitudinal portion of the object. The sensing coils are subdivided to achieve circumaxial resolution. For example, if a multitude of magnetic flux sensing coils are employed, the voltage signals IN(1) through IN(N) induced in each coil can be separately processed to more accurately determine the axial location of a structural fault.

Figure 8B:
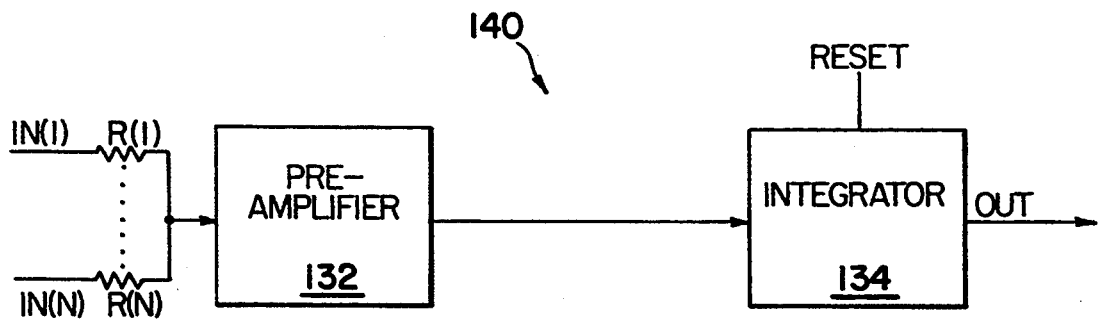
FIG. 8b is a schematic view of circuitry for adding and integrating multiple voltage signals from sensing means employed circumaxially of an object to be inspected.

FIG. 8b schematically shows an alternative approach to processing the voltage signals IN(1) through IN(N). The different approach is that the voltage signals IN(1) through IN(N) are added together through respective resistors R(1) through R(N) before being input into the integrator 134, thus providing a quantitative measurement of eddy current changes circumaxially about the elongated object.

Of course, the processing methods of FIGS. 8a and 8b may be combined so as to provide both types of structural fault data.

One problem with measuring structural faults at stagnation points along a magnetically permeable object is that unwanted random, localized permeability variations along the object may be present. Localized random permeability variations along the object can be caused, for example, by localized stress variations in wire cables and pipes. This can happen during manufacture and operation. The random permeability variations change the eddy currents within the object. At a stagnation point, the change in eddy currents originating from unwanted, random permeability variations tends to be large and to be predominant over changes originating from structural faults. Hence, random permeability variations along the object can lead to unwanted noise levels that significantly mask the detection of structural faults.

Figure 9:
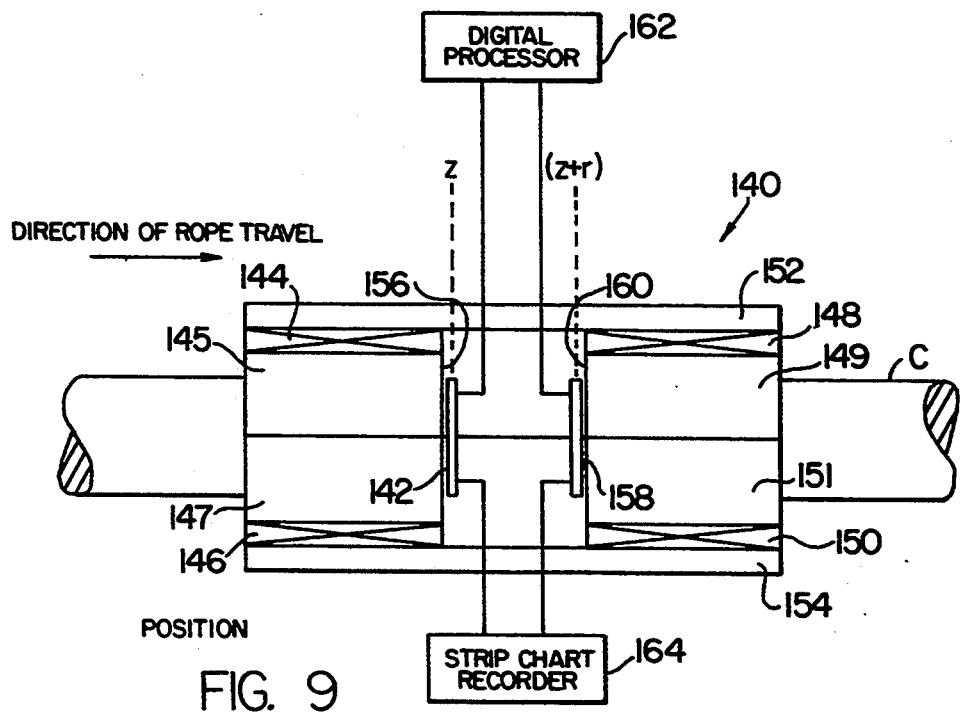
FIG. 9 schematically illustrates another embodiment of the magnetic inspection device along a longitudinal section of a metal cable.

Experiments have shown that unwanted, random permeability variations and resulting background noise can be significantly reduced by magnetically saturating (or near-saturating) the object under inspection. Then the incremental permeability of the object approaches that of air, and incremental permeability varations are drastically reduced. In the present case, this approach can be implemented by placing the eddy current change detecting means downstream from an end pole, in the direction of fault movement with the object, as schematically illustrated in FIG. 9. The operation and advantages of the embodiment of FIG. 9 are explained below.

Referring to FIG. 9, a magnetic inspection device 140 magnetically inspects for structural faults a rightwardly moving magnetically permeable elongated object such as, in this instance, a cable C. Longitudinally spaced and oppositely poled upper end pole permanent magnets 144 and 148 are adjacent respective end pole pieces 145 and 149. The upper end pole magnets 144 and 148 cooperate with one another to induce part of a longitudinal magnetic flux through the cable C. An upper ferromagnetic flux return bar 152 completes a magnetic flux circuit for the permanent magnets 144 and 148.

Similarly, longitudinally spaced and oppositely poled lower end pole permanent magnets 146 and 150 are adjacent respective end pole pieces 147 and 151. The lower end pole magnets 146 and 150 cooperate with one another to induce part of a longitudinal magnetic flux through the cable C. Permanent magnet 146 has the same polarity as that of permanent magnet 144 with respect to the object, and permanent magnet 150 has the same polarity as that of permanent magnet 148 with respect to the object so that lower permanent magnets 146 and 150 reinforce the magnetic flux induced by the upper permanent magnets 144 and 148. A lower ferromagnetic flux return bar 154 completes a magnetic flux circuit for the magnets 146 and 150.

An eddy current change detector 142 for detecting structural faults is positioned adjacent to and immediately downstream from the end poles 145 and 147, in the direction of fault movement with the object.

As the cable C moves rightwardly between the permanent end pole magnets 144 and 146, a portion of the cable C is magnetized and thereby experiences a rapid change in longitudinal magnetic flux induced therethrough as indicated in FIG. 1b by the rightwardly rising slope passing through SP1. Because of Faraday's and Lenz's laws, the rapid change in longitudinal magnetic flux through a moving portion of cable C generates eddy currents so as to oppose the change in magnetic flux. As the rightwardly moving portion passes downstream of edge 156 of the end pole 145, the moving portion is no longer under the magnetizing influence of the magnets 144,146 and is in the region of FA as illustrated in FIG. 1b. Consequently, the rightwardly moving portion of the cable of FIG. 9, now downstream of the magnets 144 and 146, no longer experiences a rapid change in the longitudinal magnetic flux therethrough and the generation of eddy currents. However, if the cable C is moving with a velocity within a range of, for example, 100 fpm to 18 mph (1584 fpm), the magnitude of the now decaying eddy currents will still be high and detectable as the rightwardly moving portion passes the adjacent eddy current change detector 142. The electromagnetic property and geometry of the magnets and flux return bars are chosen so that as a portion of cable C moves past the detector 142, the moving portion is at or approaching magnetic saturation.

When the cable C becomes magnetically saturated by the end pole magnets 144 and 146, the overall permeability of the cable decreases significantly (possibly by several orders of magnitude) and stabilizes at a permeability value approaching that of air. Because of the overall permeability stability at saturation, any unwanted random permeability variations along the cable and corresponding noise will be significantly reduced. The eddy current change detector 142 is, therefore, advantageously placed over a portion of the cable C having such a reduced and stable permeability. Hence, positioning the eddy current change detector immediately downstream of the end poles 145 and 147 where the longitudinal flux is at or approaching saturation, in contrast to the stagnation point directly under the magnets (where the longitudinal flux is near zero), significantly decreases background noise which masks the detection of structural faults.

A drawback with employing an eddy current-magnetic saturation approach is that the eddy current change detector 142 passively generates an induced signal S₁ comprising both an eddy current change signal component $s_{ec}$ and an unwanted magnetic flux change signal component $s_{mf}$. This unwanted component is the magnetic flux change characteristic of other types of faults such as loss of metallic cross-sectional area (LMA) or localized faults (LFs).

A method for determining the sec signal component resulting from a structural fault employs a magnetic flux detector 158 which passively generates an induced signal S₂ comprising eddy current signal component $s_{ec}$ as well as a magnetic flux signal component $s_{mf}$. The magnetic flux detector is preferably placed adjacent to and immediately upstream of the edge 160 of the end pole 149 in the direction of cable movement so as to be adjacent to a moving portion of the object which is at or approaching magnetic saturation. As a portion of the cable moves rightwardly, the magnetic flux detector 158 passively generates an induced signal S₂ also comprising an eddy current signal component $s_{ec}$ as well as a magnetic flux signal component $s_{mf}$. For magnetic flux detector 158, the eddy current change component is the unwanted signal. The eddy current change signal component of a structural fault generated by magnetic flux detector 158, however, will be much smaller than that generated by eddy current change detector 142 because the eddy currents have steadily decayed during cable movement from the one detector to the other detector.

Assuming linear superposition, the following equations hold:

$$S_1(z) = (a)(s_{mf}(z)) + (b)(s_{ec}(z)) \quad (1)$$

$$S_2(z+r) = (c)(s_{mf}(z+r)) + (d)(s_{ec}(z+r)) \quad (2)$$

Here, z is the longitudinal coordinate of the eddy current change detector 142, z+r is the longitudinal coordinate of the magnetic flux detector 158, and r is the absolute distance between the detectors 142 and 158. Constants a,b,c, and d of equations (1) and (2) depend on the geometry of the detectors and the magnetically permeable object. Constants b and d are also functions of the inspection velocity of the magnetic device. Equations (1) and (2) are substantially two simultaneous equations with two unknowns, $s_{ec}$ and $s_{mf}$, that can be solved for the signal components of a defect passing under the eddy current change detector 142, and later passing under the magnetic flux detector 158.

The signal components $s_{ec}$ and $s_{mf}$ can be determined by means of digital processing by a digital processor 162 communicating with the detectors 142,158. Hence, by means of digital processing, the location and magnitude of a structural fault can be determined and isolated from other types of defects such as LMA or LFs. Of course, the locations of LMA, LF and/or SF faults can also be determined.

Another reliable and simple means for locating and isolating SFs from LMA and/or LFs is through visual inspection and cross-comparison of the signals S₁ and S₂ generated and recorded by a strip chart recorder 164 which is electrically coupled to the detectors 142 and 158.

While the present invention has been described in several embodiments, it will be understood that numerous modifications and substitutions can be made without departing from the spirit of the invention. For example, the permanent magnets in the preferred embodiments can be replaced by other suitable devices such as electromagnets. Further, eddy current or magnetic flux detecting means could be any suitable means such as coils, Hall effect sensors, or coils-cum-integrators. Likewise, one or more eddy current change detecting means can be positioned near or at one and/or the other end poles in order to gather more precise data of the elongated object to be inspected. The eddy current change detecting means employed as SF sensors can also be used with a combination of LMA and LF sensors which are both normally located between longitudinally spaced opposite magnetic poles. In addition, the present invention does not preclude using a three or more pole device. The relative movement between the magnetic inspection device and object to be inspected can, of course, be produced by either moving the object relative to a stationary inspection device, by moving the device relative to a stationary object, or by moving both the device and the object in opposite directions relative to each other. Accordingly, the present invention has been described in several preferred embodiments by way of illustration, rather than limitation.

I claim:

1. A magnetic inspection device for nondestructively detecting structural faults in elongated objects, such as wire cables, rods, pipes, and the like comprising:

magnet means having two opposite magnetic poles spaced from one another for positioning at longitudinally spaced stations along an elongated magnetically permeable object and for movement longitudinally relative to the object, the magnet means defining first and second magnetic flux circuits, the first magnetic flux circuit having a forward portion extending between one pole and the other pole through a first section of the elongated object between the stations, and the first magnetic flux circuit having a return portion extending through a ferromagnetic flux return path within the magnet means, whereby a first longitudinal magnetic flux is induced in one direction generally at a magnetic saturation level through the elongated object, the second magnetic flux circuit having a forward portion extending through a second section of the elongated object lying longitudinally adjacent both the first section and the one pole, the forward portion of the second magnetic flux circuit extending in a direction opposite to that of the forward portion of the first magnetic flux circuit, the second magnetic flux circuit having a return portion externally of the elongated object, whereby a second longitudinal magnetic flux is induced in the object in a direction opposite to that of the first longitudinal magnetic flux, the junction of the two oppositely directed magnetic fluxes in a moving portion of the object confronting the one pole defining a stagnation point where the magnitude of the first and second longitudinal magnetic fluxes is zero, and where eddy currents are generated on the surface of said moving portion of the object because of change of longitudinal magnetic flux resulting from relative movement of the object and the magnet means, the generated eddy currents dissipating as said portion moves downstream in the direction of object movement from the one pole to the other pole;

eddy current change detecting means associated with the one pole for positioning longitudinally adjacent to the object where the longitudinal magnetic flux is at or approaching a magnetic saturation level and where eddy currents generated by the change of longitudinal magnetic flux have not substantially dissipated within said moving portion as said portion passes the eddy current change detecting means so as to detect longitudinal magnetic flux changes from a moving portion of the object as the portion moves past the eddy current change detecting means, whereby longitudinal magnetic flux changes experienced by said moving portion of the object passing by the eddy current change detecting means generate a first signal in the eddy current change detecting means including a first signal component originating from eddy current changes representative of structural faults and a second signal component originating from magnetic flux changes representative of loss of metallic cross-sectional area or localized faults;

magnetic flux detecting means associated with the other of the poles for positioning longitudinally downstream in the direction of object movement from the eddy current change detecting means longitudinally adjacent to the object where the longitudinal magnetic flux is at or approaching a magnetic saturation level and where the eddy currents generated by the change of longitudinal magnetic flux have substantially dissipated within said moving portion as said portion passes the magnetic flux detecting means so as to detect longitudinal magnetic flux changes experienced by said moving portion of the object passing by the magnetic flux detecting means after said portion has moved past the eddy current change detecting means, whereby longitudinal magnetic flux changes of said moving portion generate a second signal in the magnetic flux detecting means including a third signal component originating from eddy current changes representative of structural faults and a fourth signal component originating from magnetic flux changes representative of loss of metallic cross-sectional area or localized faults; and digital processing means for determining the location and magnitude of a structural fault within said moving portion from the first and second signals.

2. A magnetic inspection device as defined in claim 1 wherein the eddy current change detecting means is a magnetic flux sensing coil.

3. A magnetic inspection device as defined in claim 2 further including an electronic integrator for integrating signals from the magnetic flux sensing coil.

4. A magnetic inspection device as defined in claim 2 wherein the magnetic flux sensing coil is positioned to extend circumaxially of the elongated magnetically permeable object.

5. A magnetic inspection device as defined in claim 1 wherein:

the magnet means includes a pole piece and a magnet defining each of the magnetic poles, the pole piece being mounted within the magnet means to be positioned between the magnet and the elongated object to be inspected.

6. A magnetic inspection device as defined in claim 5 further including a plastic bushing for positioning between the pole piece and the elongated object to be inspected, said plastic bushing moving in unison with the pole piece relative to the object.

7. A magnetic inspection device as defined in claim 6 wherein the plastic bushing has an arcuate surface at a side opposite the pole piece.

8. A magnetic inspection device as defined in claim 6 wherein the plastic bushing and the pole piece have mating arcuate surfaces.

9. A magnetic inspection device as defined in claim 5 wherein the pole piece further includes a groove to extend circumaxially of the elongated object to be inspected; and the eddy current change detecting means includes a magnetic flux sensing coil mounted in the groove.

10. A magnetic inspection device as defined in claim 6 wherein the plastic bushing further includes a groove to extend circumaxially of the elongated object to be inspected; and the eddy current change detecting means includes a magnetic flux sensing coil mounted in the groove.

11. A magnetic inspection device as defined in claim 1 wherein:

the two opposite magnetic poles, at least one pole being an end pole, constitute a first set of opposite magnetic poles at the longitudinally spaced stations;

the magnet means further includes a second set of two opposite magnetic poles at the longitudinally spaced stations, at least one pole of the second set being an end pole;

the poles of the first and second sets which are positioned at diametrically opposite sides of the elongated object to be inspected have similar polarities adjacent the object at the respective stations to induce each of the opposed first and second magnetic fluxes in the object, and the end pole of the first set and the end pole of the second set are located at the same station; and the eddy current change detecting means has a first magnetic flux sensing coil which is positioned circumaxially of one portion of the elongated object to be inspected near the end pole of the first set, and a second magnetic flux sensing coil which is positioned circumaxially of another portion of the elongated object to be inspected near the end pole of the second set, the first and second magnetic flux sensing coils being connected in series to combine the detected changes in the eddy currents.

12. A magnetic inspection device as defined in claim 11, further including:

a housing defining a central passageway through which the elongated object may move longitudinally of itself during inspection, and having first and second separable housing portions defining a parting plane intersecting the central passageway along its length to permit the first and second housing portions to be mounted in mating relationship over and removed from the elongated object intermediate ends of the elongated object;

the first set of the opposite magnetic poles is supported in the first separable housing portion, and the second set of the opposite magnetic poles is supported in the second separable housing portion; and the first magnetic flux sensing coil is supported in the first separable housing portion, and the second magnetic flux sensing coil is supported in the second separable housing portion.

13. An internal magnetic inspection device for nondestructively detecting structural faults from within elongated objects, such as pipes and the like comprising:

magnet means including two opposite magnetic poles for mounting adjacent to the interior surface of an elongated object, the poles being longitudinally spaced from one another for positioning at longitudinally spaced stations adjacent the object during movement longitudinally relative to the object, the magnet means defining first and second magnetic flux circuits, the first magnetic flux circuit having a forward portion extending from one pole to the other pole through a first section of the elongated object between the stations, and a return portion through a ferromagnetic flux return path within the magnet means to be disposed at or near the central longitudinal axis of the object to be inspected and extending from the one pole to the other pole, whereby a first longitudinal magnetic flux is induced in one direction through the elongated object, the second magnetic flux circuit having a forward portion extending from the one pole through a second section of the elongated object lying longitudinally adjacent both the first section and the one pole in a direction opposite to that of the forward portion of the first magnetic flux circuit, and a return portion externally of the elongated object whereby a second longitudinal magnetic flux is induced in the object in a direction opposite to that of the first longitudinal magnetic flux, the junction of the two oppositely directed magnetic fluxes being in a moving portion of the object confronting the one pole and defining a stagnation point, and where eddy currents are generated on the surface of said moving portion of the object because of change of longitudinal magnetic flux resulting from relative movement of the object and the magnet means; and a magnetic flux sensing coil located near the one pole and close to the interior surface of the elongated object to be inspected for detecting eddy current changes representative of structural faults during relative movement of the magnet means and the object.

14. A magnetic inspection device as defined in claim 13 further including an electronic integrator for integrating signals from the magnetic flux sensing coil.

15. A magnetic inspection device as defined in claim 13 wherein the magnetic flux sensing coil is positioned to extend circumaxially of the elongated magnetically permeable object.

16. A magnetic inspection device as defined in claim 13 wherein:

the magnet means includes a pole piece and a magnet defining each of the magnetic poles, the pole piece being mounted within the magnet means for positioning between the magnet and the elongated object to be inspected.

17. A magnetic inspection device as defined in claim 16 wherein the pole piece further includes a groove to extend circumaxially of the elongated object to be inspected; and the magnetic flux sensing coil is mounted in the groove.

18. A method for nondestructively inspecting an elongated magnetically permeable object, such as wire cables, rods, pipes, and the like for structural faults, comprising the steps of:

inducing a first magnetic flux in one direction generally at a saturation level by means of a magnet device through a first longitudinal section of an elongated object, the longitudinal section extending between first and second longitudinally spaced opposite poles of the magnet device;

inducing a second magnetic flux through a second longitudinal portion of the object longitudinally adjacent the first longitudinal portion by means of the magnet device, the second magnetic flux being opposite in direction to that of the first magnetic flux, the junction of the first and second magnetic fluxes in the object being longitudinally adjacent to the first pole and defining a stagnation point;

moving the magnet device and the induced first and second magnetic fluxes progressively and longitudinally relative to the object so as to induce circumaxial eddy currents in a moving portion of the object passing the first pole due to the change in the magnetic fluxes within said moving portion of the magnetically permeable object at the first pole of the magnet device, the first pole of the magnet device being longitudinally upstream from the second pole of the magnet device relative to movement of the object;

generating a first signal from said moving portion of the object when said portion is immediately longitudinally downstream from the first pole of the magnet device in the direction of movement of the object during the moving step, said portion during the step of generating a first signal being at or approaching a magnetic saturation level and including substantial eddy currents, the first signal including a first signal component originating from eddy current changes representative of structural faults and a second signal component originating from magnetic flux changes representative of loss of metallic cross-sectional area or localized faults; and subsequently generating a second signal from said moving portion of the object when said portion is immediately longitudinally upstream from the second pole of the magnet device in the direction of movement of the object during the moving step, said portion during the step of generating a second signal being at or approaching a magnetic saturation level and including eddy currents which have substantially dissipated during the time elapsed from the step of generating a first signal, the second signal including a third signal component originating from eddy current changes and a fourth signal component originating from magnetic flux changes; and determining the location and magnitude of a structural fault within said moving portion from the first and second signals.

19. A method for nondestructively inspecting an elongated magnetically permeable object as defined in claim 18, further including the step of integrating eddy current changes through an electronic integrator.

20. A method for nondestructively inspecting an elongated magnetically permeable object as defined in claim 18, wherein the steps of generating the first and second signals from the object include employing magnetic flux sensing coils extending circumaxially of the elongated object to be inspected.

21. A method for inspecting an elongated magnetically permeable object as defined in claim 18, wherein the steps of inducing the first and second magnetic fluxes are achieved by employing plural sets of opposite poles disposed about the object, and by closing a first magnetic circuit within the magnet device through a plurality of ferromagnetic flux return paths disposed about the elongated object and associated respectively with the sets of poles; and the steps of generating the first and second signals from the object include employing for each of said signals a plurality of magnetic flux sensing coils extending circumaxially of the elongated object, each of the magnetic flux sensing coils corresponding to one set of the opposite magnetic poles.

22. A method for inspecting an elongated magnetically permeable object as defined in claim 18, wherein the steps of inducing the first and second magnetic fluxes are achieved by employing plural sets of opposite poles disposed about an inner surface of the object, and by closing a first magnetic circuit within the magnet device through a common ferromagnetic flux return path located along the longitudinal axis at the center of the elongated object; and the steps of generating the first and second signals from the object include employing for each of said signals a plurality of magnetic flux sensing coils extending circumaxially of the inner surface of the elongated object, each of the magnetic flux sensing coils corresponding to a set of the opposite magnetic poles.

23. A magnetic inspection device for nondestructively detecting structural faults in elongated objects, such as wire cables, rods, pipes, and the like comprising:

magnet means having two opposite magnetic poles spaced from one another for positioning at longitudinally spaced stations along an elongated magnetically permeable object and for movement longitudinally relative to the object, the magnet means defining first and second magnetic flux circuits, the first magnetic flux circuit having a forward portion extending between one pole and the other pole through a first section of the elongated object between the stations, and the first magnetic flux circuit having a return portion extending through a ferromagnetic flux return path within the magnet means, whereby a first longitudinal magnetic flux is induced in one direction generally at a magnetic saturation level through the elongated object, the second magnetic flux circuit having a forward portion extending through a second section of the elongated object lying longitudinally adjacent both the first section and the one pole, the forward portion of the second magnetic flux circuit extending in a direction opposite to that of the forward portion of the first magnetic flux circuit, the second magnetic flux circuit having a return portion externally of the elongated object, whereby a second longitudinal magnetic flux is induced in the object in a direction opposite to that of the first longitudinal magnetic flux, the junction of the two oppositely directed magnetic fluxes in a moving portion of the other confronting the one pole defining a stagnation point where the magnitude of the first and second longitudinal magnetic fluxes is zero, and where eddy currents are generated on the surface of said moving portion of the object because of change of longitudinal magnetic flux resulting from relative movement of the object and the magnet means, the generated eddy currents dissipating as said portion moves longitudinally downstream in the direction of object movement from the one pole to the other pole;

eddy current change detecting means located between the two opposite poles and longitudinally adjacent the one pole for positioning adjacent to the object where the longitudinal magnetic flux is at or approaching a magnetic saturation level so as to detect longitudinal magnetic flux changes from a moving portion of the object as the portion moves past the eddy current change detecting means, whereby longitudinal magnetic flux changes experienced by said moving portion of the object passing by the eddy current change detecting means generate a first signal in the eddy current change detecting means including a first signal component originating from eddy current changes representative of structural faults and a second signal component originating from magnetic flux changes representative of loss of metallic cross-sectional area or localized faults;

magnetic flux detecting means located between the two opposite poles and longitudinally adjacent to the other of the poles for positioning adjacent to the object where the longitudinal magnetic flux is at or approaching a magnetic saturation level and where the eddy currents generated by the change of longitudinal magnetic flux have substantially dissipated within said moving portion as said portion passes the magnetic flux detecting means so as to detect longitudinal magnetic flux changes experienced by said moving portion of the object passing by the magnetic flux detecting means after said portion has moved past the eddy current change detecting means, whereby longitudinal magnetic flux changes of said moving portion generate a second signal in the magnetic flux detecting means including a third signal component originating from eddy current changes representative of structural faults and a fourth signal component originating from magnetic flux changes representative of loss of metallic cross-sectional area or localized faults; and digital processing means for determining the location and magnitude of a structural fault within said moving portion from the first and second signals.

24. A magnetic inspection device for nondestructively detecting structural faults in elongated objects, such as wire cables, rods, pipes, and the like comprising:

magnet means having two opposite magnetic poles spaced from one another for positioning at longitudinally spaced stations along an elongated magnetically permeable object and for movement longitudinally relative to the object, the magnet means defining first and second magnetic flux circuits, the first magnetic flux circuit having a forward portion extending between one pole and the other pole through a first section of the elongated object between the stations, and the first magnetic flux circuit having a return portion extending through a ferromagnetic flux return path within the magnet means, whereby a first longitudinal magnetic flux is induced in one direction generally at a magnetic saturation level through the elongated object, the second magnetic flux circuit having a forward portion extending through a second section of the elongated object lying longitudinally adjacent both the first section and the one pole, the forward portion of the second magnetic flux circuit extending in a direction opposite to that of the forward portion of the first magnetic flux circuit, the second magnetic flux circuit having a return portion externally of the elongated object, whereby a second longitudinal magnetic flux is induced in the object in a direction opposite to that of the first longitudinal magnetic flux, the junction of the two oppositely directed magnetic fluxes in a moving portion of the object confronting the one pole defining a stagnation point where the magnitude of the first and second longitudinal magnetic fluxes is zero, and where eddy currents are generated on the surface of said moving portion of the object because of change of longitudinal magnetic flux resulting from relative movement of the object and the magnet means, the generated eddy currents dissipating as said portion moves longitudinally downstream in the direction of object movement from the one pole to the other pole;

eddy current change detecting means located between the two opposite poles immediately longitudinally downstream from the one pole in the direction of movement of the object relative to the magnet means, said eddy current change detecting means for positioning longitudinally adjacent to the object where the longitudinal magnetic flux is at or approaching a magnetic saturation level and where eddy currents generated by the change of longitudinal magnetic flux have not substantially dissipated within said moving portion as said portion passes the eddy current change detecting means so as to detect longitudinal magnetic flux changes from a moving portion of the object as the portion moves past the eddy current change detecting means, whereby longitudinal magnetic flux changes experienced by said moving portion of the object passing by the eddy current change detecting means generate a first signal in the eddy current change detecting means including a first signal component originating from eddy current changes representative of structural faults and a second signal component originating from magnetic flux changes representative of loss of metallic cross-sectional area or localized faults;

magnetic flux detecting means located between the two opposite poles immediately longitudinally upstream from the other of the opposite poles in the direction of movement of the object relative to the magnet means, said magnetic flux detecting means for positioning longitudinally downstream in the direction of object movement from the eddy current change detecting means adjacent to the object where the longitudinal magnetic flux is at or approaching a magnetic saturation level and where the eddy currents generated by the change of longitudinal magnetic flux have substantially dissipated within said moving portion as said portion passes the magnetic flux detecting means so as to detect longitudinal magnetic flux changes experienced by said moving portion of the object passing by the magnetic flux detecting means after said portion has moved past the eddy current change detecting means, whereby longitudinal magnetic flux changes of said moving portion generate a second signal in the magnetic flux detecting means including a third signal component originating from eddy current changes representative of structural faults and a fourth signal component originating from magnetic flux changes representative of loss of metallic cross-sectional area or localized faults; and digital processing means for determining the location and magnitude of a structural fault within said moving portion from the first and second signals.

* * * * *